US 12,234,443 B2

(12) United States Patent
Sato et al.

(10) Patent No.: US 12,234,443 B2
(45) Date of Patent: Feb. 25, 2025

(54) CELL RECOVERY APPARATUS, CELL RECOVERY METHOD, CELL SEPARATION SYSTEM, AND CELL SEPARATION METHOD

(71) Applicant: RESONAC CORPORATION, Tokyo (JP)

(72) Inventors: Yushi Sato, Tokyo (JP); Masahiro Okanojo, Tokyo (JP); Shangwu Chen, Tokyo (JP); Katsuhiko Nakashima, Tokyo (JP); Ryosuke Takahashi, Tokyo (JP); Yasuhiko Tada, Tokyo (JP)

(73) Assignee: Resonac Corporation, Tokyo (JP)

( * ) Notice: Subject to any disclaimer, the term of this patent is extended or adjusted under 35 U.S.C. 154(b) by 913 days.

(21) Appl. No.: 17/418,936

(22) PCT Filed: Dec. 15, 2020

(86) PCT No.: PCT/JP2020/046697
§ 371 (c)(1),
(2) Date: Jun. 28, 2021

(87) PCT Pub. No.: WO2021/181784
PCT Pub. Date: Sep. 16, 2021

(65) Prior Publication Data
US 2022/0306980 A1    Sep. 29, 2022

(30) Foreign Application Priority Data
Mar. 11, 2020  (JP) ................................. 2020-042322

(51) Int. Cl.
*C12M 1/00*  (2006.01)
*C12M 1/12*  (2006.01)
(Continued)

(52) U.S. Cl.
CPC .............. *C12M 47/02* (2013.01); *C12M 3/06* (2013.01); *C12M 25/16* (2013.01); *C12M 33/14* (2013.01)

(58) Field of Classification Search
CPC ........ C12M 47/02; C12M 3/06; C12M 25/16; C12M 33/14
See application file for complete search history.

(56) References Cited

U.S. PATENT DOCUMENTS

| 9,713,669 B2 | 7/2017 | Wegener et al. |
| 2005/0196828 A1 | 9/2005 | Zheng et al. |

(Continued)

FOREIGN PATENT DOCUMENTS

| JP | H05-168471 A | 7/1993 |
| JP | H08-172956 A | 7/1996 |

(Continued)

OTHER PUBLICATIONS

Matsuura et al., "Adequate taylor couette flow-mediated shear stress is useful for dissociating human iPS cell-derived cell aggregates," Regenerative Therapy, 12: 6-13 (2019).

*Primary Examiner* — Michael L Hobbs
(74) *Attorney, Agent, or Firm* — Morgan, Lewis & Bockius LLP (57) ABSTRACT

Apparatus, system, and method are disclosed for cell recovery or cell separation. A cell separation system has at least a first container having a first filter for separating a first removal target from a suspension comprising cells and a removal target including at least the first removal target and a second removal target; a cell separation apparatus; a first flow path connecting the first container and the cell separation apparatus; and a first pump interposed in the first flow path for transferring the suspension from the first container to the cell separation apparatus by decompression suction, for example.

19 Claims, 5 Drawing Sheets

(51) Int. Cl.
    *C12M 1/26*     (2006.01)
    *C12M 3/06*     (2006.01)

(56) References Cited

U.S. PATENT DOCUMENTS

| | | | |
|---|---|---|---|
| 2013/0115588 A1 * | 5/2013 | Davis | C12M 33/14 |
| | | | 435/286.1 |
| 2015/0182682 A1 | 7/2015 | Wegener et al. | |
| 2019/0099540 A1 | 4/2019 | Smith et al. | |
| 2019/0099545 A1 | 4/2019 | Wegener et al. | |
| 2019/0169572 A1 | 6/2019 | Shi et al. | |
| 2021/0087512 A1 | 3/2021 | Ikeda et al. | |

FOREIGN PATENT DOCUMENTS

| | | | | |
|---|---|---|---|---|
| JP | 2005-536225 A | | 12/2005 | |
| JP | 2009072129 A | * | 4/2009 | ............ C12M 27/02 |
| JP | 2015123060 A | * | 7/2015 | ............ C12M 33/00 |
| JP | 2015-164414 A | | 9/2015 | |
| JP | 2019-509763 A | | 4/2019 | |
| JP | 2019-080562 A | | 5/2019 | |
| JP | 2019-0140985 A | | 8/2019 | |
| JP | 2019-213497 A | | 12/2019 | |
| WO | 2012/002497 A1 | | 1/2012 | |
| WO | 2017/112455 A2 | | 6/2017 | |

* cited by examiner

CELL RECOVERY APPARATUS, CELL RECOVERY METHOD, CELL SEPARATION SYSTEM, AND CELL SEPARATION METHOD

TECHNICAL FIELD

The technology in the present disclosure relates to cell recovery apparatus, cell recovery method, cell separation system, and cell separation method.

BACKGROUND

In biomedical research and clinical practice, samples taken from a subject are cultured in vitro, and then the target samples (for example, cells and humoral factors) are selected and recovered for use in subsequent research and treatment. For example, in the field of regenerative medicine and cell therapy, after cells collected from a subject are grown in a medium, undesired cells and contaminants are separated from the medium, and the target cells and humoral factors are recovered and used (for example, U.S. Patent Publication No. 2019/0169572, Japanese Patent Publication 2019-509763, et al.).

In the recovery of cells, in addition to the recovery of cells with high purity, the maintenance of cell quality is required in order to improve the quality of subsequent treatment and research. In particular, microbial contamination that could alter the biochemical and molecular properties of the target cells must be avoided. Therefore cells need to be handled under sterile conditions.

SUMMARY

Technical Problem

Accordingly, it is the purpose of the disclosure to provide a cell recovery apparatus and a cell recovery method capable of handling a target cell in a sterile condition by various embodiments. Another purpose of the disclosure is to provide a cell separation system and a cell separation method capable of separating and recovering cells with high purity.

Solution to Problem

A cell recovery apparatus according to one aspect of the disclosed technology comprises a first container having a first filter for separating cells from a suspension containing the cells; a recovery container connected to the first container by a first flow path; a first pump, which is a positive displacement pump interposed in the first flow path, and transfers the separated cells from the first container to the recovery container by decompression suction; a second container disposed on the upstream side of the first container; a second flow path connecting the second container and the first container; a second pump for transferring the suspension from the second container to the first container via the second flow path; and a third flow path connecting the second pump and the second container; wherein the first container, the first flow path, the recovery container, the first pump, the second container and the second flow path are connected in a closed system.

In addition, the cell recovery apparatus according to one aspect further comprises a second filter interposed in the third flow path. Further, with regard to the cell recovery apparatus according to one aspect, the second pump is a pump in the manner of applying pressure by gas. Further, with regard to the cell recovery apparatus according to one aspect, the cells are supported on carriers in the suspension; the cells are detached from the carriers on the upstream side of the first filter; and the cells and the carriers are separated by the first filter.

In addition, with regard to the cell recovery apparatus according to one aspect, the first container comprises at least one selected from the group consisting of a shaker, a stirrer, and a centrifuge. Further, with regard to the cell recovery apparatus according to one aspect, the second container comprises at least one selected from the group consisting of a shaker and a stirrer. Further, with regard to the cell recovery apparatus according to one aspect, the second filter has a pore diameter in the range of 0.01 μm to 30 μm.

In addition, with regard to the cell recovery apparatus according to one aspect, the cells supported on the carriers are detached from the carriers in the second container. Further, with regard to the cell recovery apparatus according to one aspect, the flow rate of the first flow path is in the range of 0.0004 L/min to 8.0 L/min. Further, with regard to the cell recovery apparatus according to one aspect, the first flow path has an inner diameter in the range of 1.8 mm to 13.0 mm. Further, with regard to the cell recovery apparatus according to one aspect, the first flow path has an outer diameter in the range of 2.0 mm to 16.0 mm.

A cell recovery method according to one aspect of the disclosed technology comprises transferring a suspension comprising cells from a second container to a first container by a second pump; separating the cells from the suspension in the first container; and transferring the separated cells from the first container to a recovery container by decompression suction of a first pump which is a positive displacement pump, wherein the transfer of the suspension from the second container to the first container, the separation of the cells, and the transfer of the separated cells to the recovery container are carried out in a closed system.

In addition, with respect to the cell recovery method according to one aspect, the second pump is a pump in the manner of applying pressure by gas. In addition, the cell recovery method according to one aspect further comprises detaching the cells from carriers in the suspension comprising the carriers and the cells supported on the carriers. Further, with respect to the cell recovery method according to one aspect, the detachment of the cells, the transfer of the suspension from the second container to the first container, the separation of the cells, and the transfer of the separated cells to the recovery container are carried out in that order. Further, with respect to the cell recovery method according to one aspect, the separation is separating the cells from the suspension while shaking or agitating the first container or separating the cells from the suspension after shaking or agitating the first container.

A cell separation system according to one aspect of the disclosed technology comprises a first container having a first filter for separating a first removal target from a suspension comprising cells and a removal target including at least the first removal target and a second removal target; a cell separation apparatus; a first flow path connecting the first container and the cell separation apparatus; and a first pump interposed in the first flow path for transferring the suspension from the first container to the cell separation apparatus by decompression suction, wherein the cell separation apparatus comprises an outer cylinder, and an inner cylinder accommodated inside the outer cylinder having a side wall on which a large number of pores are formed, and wherein the cell separation apparatus is configured to separate the second removal target and the cells in a storage region between an inner wall of the outer cylinder and the side wall of the inner cylinder.

In addition, with respect to the cell separation system according to one aspect, the first container, the cell separation apparatus, the first flow path, and the first pump are connected in a closed system. In addition, the cell separation system according to one aspect further comprises a second container disposed on the upstream side of the first container; a second flow path connecting the second container and the first container; a second pump for transferring the suspension from the second container to the first container via the second flow path; and a third flow path connecting the second pump and the second container. Further, with respect to the cell separation system according to one aspect, the first pump is a positive displacement pump.

In addition, with respect to the cell separation system according to one aspect, the second removal target includes at least a dissolvable carrier. Further, with respect to the cell separation system according to one aspect, the cell separation apparatus separates the cells by relatively rotating the inner cylinder to the outer cylinder and transferring the second removal target from the storage region to the inside of the inner cylinder via the side wall. Further, with respect to the cell separation system according to one aspect, the relative rotation includes a first relative rotation performed at a first rotational speed and a second relative rotation performed at a second rotational speed different from the first rotational speed. Further, with respect to the cell separation system according to one aspect, the first rotational speed is faster than the second rotational speed.

A cell separation method according to one aspect of the disclosed technology comprises separating a first removal target from a suspension provided in a first container having a first filter, wherein the suspension comprises cells and a removal target including at least the first removal target and a second removal target; supplying the suspension to a storage region in a cell separation apparatus configured between a first surface and a second surface facing the first surface on which a large number of pores are formed; and separating the cells from the suspension by moving one of the first surface and the second surface relative to the other.

In addition, with respect to the cell separation method according to one aspect, the separation of the cells includes rotating one of the first surface and the second surface relative to the other so as to transfer the second removal target in the suspension to the outside of the storage region via the second surface and leave the cells in the storage region. Further, with respect to the cell separation method according to one aspect, the separation of the cells includes transferring a portion of the second removal target to the outside of the storage region by rotating one of the first surface and the second surface relative to the other at a first rotational speed; and transferring the remainder of the second removal target to the outside of the storage region by rotating one of the first surface and the second surface relative to the other at a second rotational speed. Further, with respect to the cell separation method according to one aspect, the first rotational speed is faster than the second rotational speed.

In addition, the cell separation method according to one aspect further comprises transferring the suspension from the first container to the cell separation apparatus by decompression suction of a first pump. Further, with respect to the cell separation method according to one aspect, the second removal target includes at least a dissolvable carrier.

Advantageous Effects

According to various embodiments, a cell recovery apparatus and a cell recovery method capable of handling cells in a sterile condition can be provided. Further, according to various embodiments, a cell separation system and a cell separation method capable of separating and recovering cells with high purity can be provided.

DETAILED DESCRIPTION

In the following, various embodiments will be described with reference to the accompanied drawings. Additionally, common elements as shown in drawings are assigned with a same reference sign. Also, it should be noted that there are cases where an element as shown in one drawing is omitted in another drawing for the purposes of explanation. Further, it should be noted that the accompanied drawings are not necessarily described to scale.

1. Configuration of a Cell Recovery Apparatus

Figure 1:
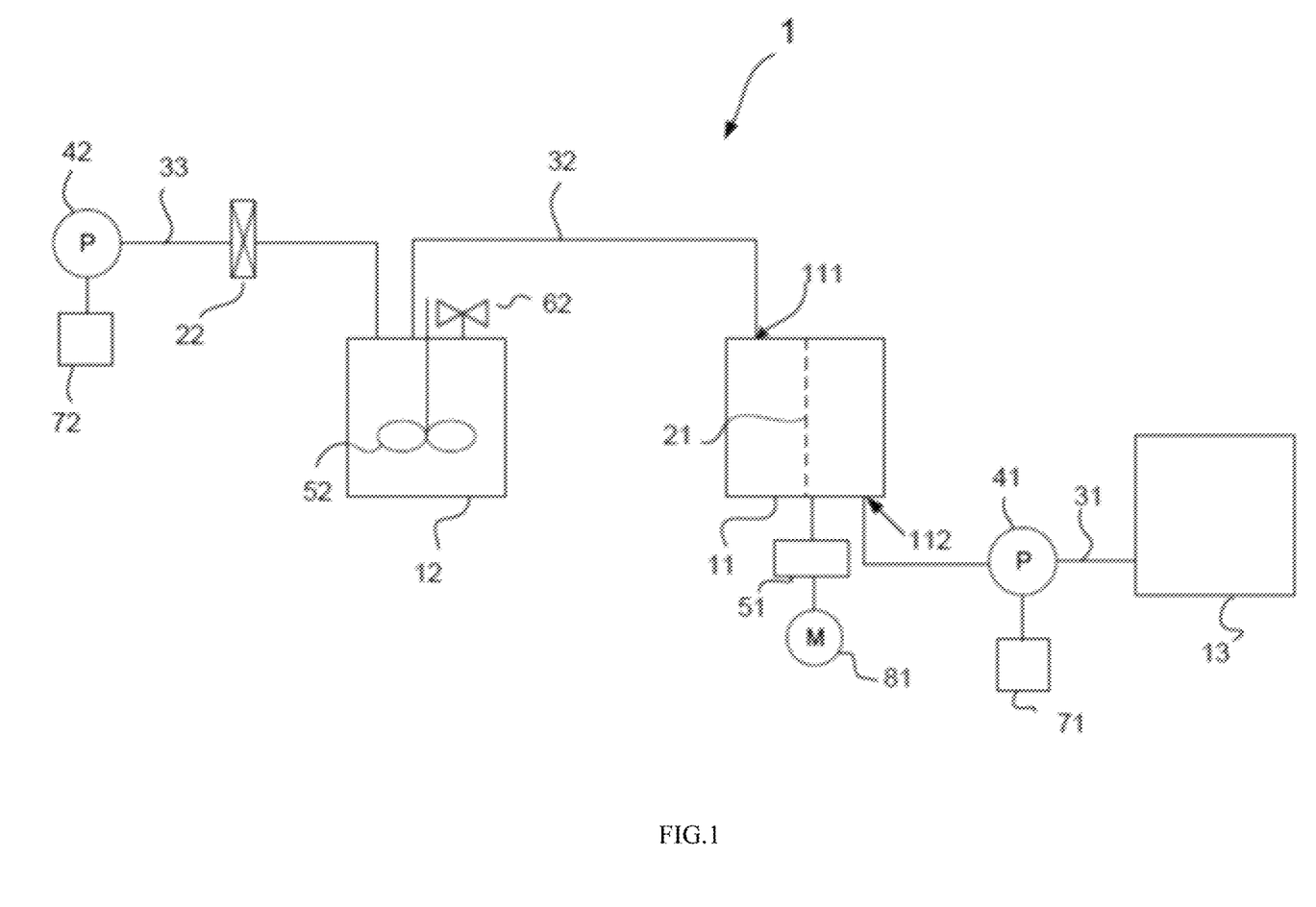
FIG. 1 is a diagram schematically showing an example of a configuration of a cell recovery apparatus according to an embodiment.

FIG. 1 is a diagram schematically showing an example of a configuration of a cell recovery apparatus 1 according to an embodiment. The example of cells provided to the cell recovery apparatus 1 include, but are not limited to, mesenchymal stem cells, induced pluripotent stem cells (iPS cells), embryonic stem cells (ES cells), Chinese hamster ovary cells (CHO cells), Vero cells, and the like. The main components of the cell recovery apparatus 1 shown in FIG. 1 are a first container 11, a first flow path 31, a recovery container 13, a first pump 41, a second flow path 32, a second container 12, a third flow path 33, and a second pump 42.

As shown in FIG. 1, containers of the cell recovery apparatus 1 are arranged in the order of the second container 12, the first container 11, and the recovery container 13 from the upstream side. The first container 11 and the recovery container 13 are connected by a first flow path 31, and a first pump 41 as a positive displacement pump is interposed in the first flow path 31. The second container 12 and the first container 11 are connected by a second flow path 32, and the second container 12 and the second pump 42 are connected by a third flow path 33.

The first container 11 has a first filter 21, a supply port 111 to which a suspension containing cells is supplied, and a discharge port 112 through which the cells are discharged. In the cell recovery apparatus 1, the suspension containing cells is transferred from the second container 12 to the second flow path 32 and supplied into the first container 11 from the supply port 111. Then, the suspension containing the cells is filtered by the first filter 21 to separate the target cells. The separated cells are discharged from the discharge port 112 to the outside of the first container 11.

The filtration of the suspension by the first filter 21 may employ a gravity filtration method by using gravity, but decompression suction by the first pump 41 and/or application of pressure by the second pump 42 may be used to speed up the filtration. In addition, a shaker or stirrer may be used to speed up the filtration speed.

The shape of the pore of the first filter 21 may be any shape as long as the target cells can be filtered or the target cells and carriers can be separated. Examples of the pore shape of the first filter 21 include a circular shape, an elliptical shape, a rectangular shape, a polygonal shape, and the like. In the present disclosure, the pore diameter means the diameter when the shape of the pore of the first filter 21 is circular, and means the length of the longest straight line among arbitrary straight lines passing through the center point of the pore in the cross section of the pore when the shape of the pore of the first filter 21 is other than circular.

The pore diameter of the first filter 21 may be appropriately selected in consideration of the size of a target cell to be recovered and the size of a carrier to be described later. For example, the pore diameter of the first filter 21 is larger than the longest diameter of the target cell and smaller than the shortest diameter of the carrier. The pore diameter of the first filter 21 is, for example, in the range of 20 μm to 100 μm, but is not limited to this range.

In one embodiment, if the size of the target cells is in the range of 12 μm to 16 μm and the size of the carrier is 200 μm, a first filter 21 having the pore diameter of 50 μm is used.

The first filter 21 divides the first container 11 into two spaces, and the supply port 111 is provided in one of the divided two spaces and the discharge port 112 is provided in the other. The suspension containing the cells is supplied from the supply port 111 to one space in the first container 11, and the target cells contained in the suspension are separated through the first filter 21 and moved to the other space. The separated target cells are discharged from the discharge port 112 to the outside of the first container 11. In this way, since the supply port 111 and the discharge port 112 are located in separate spaces divided by the first filter 21, cell separation and cell discharge can be performed smoothly.

The first container 11 may include a shaker 51 driven by a motor 81. Shaking the first container 11 prevents aggregation of target cells, contaminants and carriers, and facilitates the filtering function of the first filter 21. The first container 11 may be shaken manually. Manual shaking may improve the recovery of the target cells compared to shaking with a shaker. The shaking by the shaker 51 may be combined with the manual shaking.

The first container 11 may include a stirrer and/or a centrifuge in addition to/or instead of the shaker 51. These devices can also prevent aggregation of cells, contaminants and carriers and facilitate filtration by the first filter 21. The shaker 51, stirrer and centrifuge may be driven by the motor 81 when the suspension is supplied into the first container 11, when the cells are separated into the first container 11, and when the cells are discharged from the first container 11.

Figure 2:
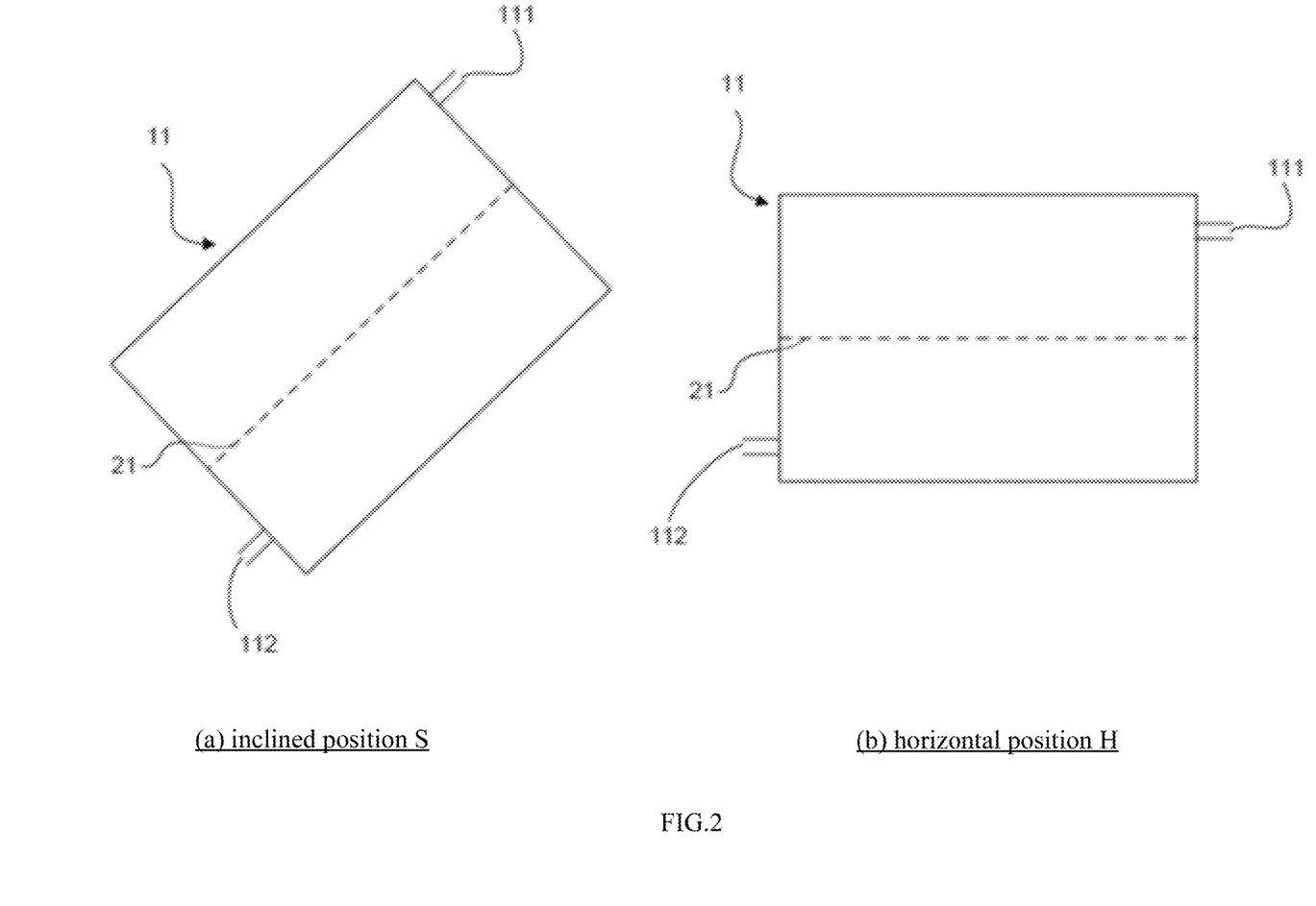
FIG. 2 is a diagram schematically showing an example of an arrangement of the first container shown in FIG. 1.

As shown in FIG. 2, the first container 11 is preferably provided so as to be capable of changing the posture between the horizontal position H and the inclined position S in one embodiment. The horizontal position H means a position where the first filter 21 is parallel to the ground, and the inclined position S means a position where the first filter 21 presents a predetermined angle (excluding 0° and 180°) with respect to the ground. When the suspension containing the cells is transferred from the second container 12 and supplied from the supply port 111 of the first container 11, the first container 11 is arranged in the posture of the inclined position S. The predetermined angle in the inclined position S includes an angle in any direction formed by the first filter 21 with respect to the ground, and may be, for example, greater than 0° and within 90° or less, greater than 0° and within 60° or less, or greater than 0° and within 45° or less.

When the cells are discharged from the discharge port 112 of the first container 11 and transferred to the recovery container 13, the first container 11 is arranged in the posture of the horizontal position H. When the cells are separated in the first container 11, the posture can be appropriately changed between the inclined position S and the horizontal position H. Further, with respect to the first container 11, while changing the posture between the inclined position S and the horizontal position H, the first container 11 may be manually shaken (and/or shaken by shaker 51) in an arbitrary direction at the same time or before or after changing the posture.

As described above, by changing the posture of the first container 11, the target cells can be efficiently separated and transferred.

The cells separated by the first filter 21 are discharged from the cell discharge port 112 by decompression suction of the first pump 41 interposed in the first flow path 31 and transferred to the recovery container 13 via the first flow path 31.

As the first pump 41, a general positive displacement pump can be used. In the present disclosure, the term "positive displacement pump" refers to a pump that is highly quantitative and has a substantially constant volume of transferred object that is sucked and/or discharged per operation. Specifically, in the positive displacement pump, when a predetermined amount of the object to be transferred is sucked at an inlet portion of the pump and then the sucked object to be transferred is discharged from an outlet portion of the pump, the volume of the suction and/or discharge is constant for each operation. By using a positive displacement pump, the target cells can be transferred in a fixed amount. As the first pump 41, for example, a general tube pump or the like can be used. The object to be transferred to the first pump 41 may contain a liquid in addition to cells.

The first flow path 31 has an inner diameter in the range of 1.0 mm to 15.0 mm and/or an outer diameter in the range of 1.5 mm to 20.0 mm, for example, and preferably has an inner diameter in the range of 1.8 mm to 13.0 mm and/or an outer diameter in the range of 2.0 mm to 16.0 mm. The provision of such a range of inner and/or outer diameters of the first flow path 31 prevents the stress from the first flow path 31 from destroying the target cells or impairing the function of the cells during transferring. In one preferred embodiment, the material of the first flow path 31 is flexible. The material of the first flow path 31 may be, for example, a thermoplastic elastomer such as an olefinic-based, a styrenic-based, a vinyl chloride-based, a urethane-based, a polyester-based, a polyamide-based, and the like, or a silicone, but the present invention is not limited thereto.

The flow rate of the first flow path 31 (that is, the rate of liquid delivery to the recovery container 13) is adjustable by a first controller 71 connected to the first pump 41 and is a flow rate of, for example, 0.0004 L/min to 8.0 L/min, preferably 0.001 L/min to 6.0 L/min, more preferably 0.1 L/min to 4.0 L/min, and most preferably 1.0 L/min to 2.5 L/min. When the flow rate of the first flow path 31 is within the above range, the cells can be transferred to the recovery container 13 while preventing the target cells from being destroyed or the functions of the cells from being impaired by decompression suction of the first pump 41.

The second container 12 has a stirrer 52. The stirrer 52 stirs the suspension containing the cells to prevent formation of aggregates in the suspension or to disaggregate the formed aggregates to facilitate transferring of the suspension to the first container 11 through the second flow path 32.

The second container 12 may have a shaker in addition to or instead of the stirrer 52. The shaker can also prevent the formation of aggregates in the suspension or deaggregate the formed aggregates to facilitate transferring of the suspension to the first container 11. The stirrer 52 and the shaker may be driven by a motor (unillustrated).

The second container 12 has a valve 62. The valve 62 ensures that the second container 12 is connected to the closed system.

In one embodiment, the cells are supported on carriers in a suspension. Here, the carrier is known, for example, as a microcarrier used in suspension culture of cells, for example, in the form of beads of several hundred micrometers in diameter. When the target cells are cultured, the cells can be obtained with a high culture area and high density by adhering the cells to beads suspended in the culture medium and proliferating them. If the cells are supported on carriers, the cells are detached from the carriers in the second container 12. Thereafter, the cells and the carriers are separated by the first filter 21 after being transferred to the first container 11.

The material of the carrier may be an organic substance, an inorganic substance or a composite material thereof, and may be either dissolvable or indissolvable. Examples of the organic substance include, but are not limited to, synthetic polymers such as polystyrene, polyester, polyurethane, polyethylene, polypropylene, polyvinyl alcohol, (meta)acrylic polymers, (meta)acrylamide polymers, silicone polymers, epoxy resins, urethane resins, and the like, and natural polymers such as cellulose, dextran, collagen, polygalacturonic acid, polyalginic acid, gelatin, and the like. Examples of the inorganic substance include, but are not limited to, glass, ceramic, metal, alloy, metal oxide, and the like. As one preferred embodiment, a carrier containing at least polystyrene is used as the carrier. As the dissolvable carrier, a natural polymer is preferably used, and, more preferably, one composed of at least one selected from the group consisting of cellulose, dextran, collagen, and polygalacturonic acid can be used.

Detachment of the cells from the carrier can be accomplished by dissolution by enzymes of the binding of the carrier to the cell. When the carrier is alginic acid or the like, the enzyme used for dissolution is trypsin.

A cell-adhesive peptide such as collagen, laminin, fibronectin, vitronectin and the like may be bonded to the carrier to improve adhesion between the cell and the carrier.

In the cell recovery apparatus 1, the first container 11, the first flow path 31, the recovery container 13, the first pump 41, the second flow path 32, and the second container 12 are connected in a closed system. In the present disclosure, the term "connected in a closed system" means that the components are connected to each other so as not to allow the movement of any substance (except for gas) to and from the outside. More specifically, the term "connected in a closed system" means that the components are connected to each other so as not to allow the movement of at least microorganisms to and from the outside, and preferably not to allow the movement of microorganisms and impurities to and from the outside.

The second pump 42 is arranged on the upstream side of the second container 12, and the second pump 42 and the second container 12 are connected by the third flow path 33.

The second pump 42 is connected to the second controller 72 and transfers the suspension containing the cells from the second container 12 to the first container 11 via the second flow path 32. The second pump 42 transfers the suspension containing the cells to the first container 11 via the second flow path 32, for example, by applying pressure into the second container 12 through the third flow path 33.

The second pump 42 is driven by the second controller 72 such that the rate of delivery of the suspension to the first container 11 is a flow rate in the range of, for example, 0.0004 L/min to 8.0 L/min, preferably 0.001 L/min to 6.0 L/min, more preferably 0.1 L/min to 4.0 L/min, and most preferably 1.0 L/min to 2.5 L/min. The flow rate to the first container 11 may be the same as or different from the flow rate in the first flow path 31.

The second pump 42 may be a non-positive displacement pump or a positive displacement pump. As the second pump 42, for example, an air pump can be used. An "air pump" is a pump that applies pressure by gas. The air pump typically operates to draw air from an inlet portion of the pump and to eject air from an outlet portion of the pump. That is, when the second pump 42 is an air pump, the air pump applies pressure by gas into the second container 12 to transfer the suspension containing the cells to the first container 11.

After transferring the suspension containing the cells to the first container 11, a washing liquid may be further transferred, by the second pump 42, to the first container 11 by providing the washing liquid in the second container 12.

The second filter 22 is interposed in the third flow path 33. By interposing the second filter 22 in the third flow path 33, it is possible to prevent microorganisms, impurities, and the like from entering the closed system from the third flow path 33 when the second pump 42 applies pressure.

The shape of the pore of the second filter 22 may be any shape as long as it can prevent at least contamination of microorganisms into the closed system, preferably contamination of microorganisms and impurities into the closed system. Examples of the shape of the pore of the second filter 22 include a circular shape, an elliptical shape, a rectangular shape, a polygonal shape, and the like. In the present disclosure, the pore diameter means the diameter when the shape of the pore of the second filter 22 is circular, and means the length of the longest straight line among arbitrary straight lines passing through the center point of the pore in the cross section of the pore when the shape of the pore of the second filter 22 is other than circular.

The pore diameter of the second filter 22 is in the range of, for example, 0.01 μm to 30.0 μm. The second filter 22 is, for example, a sterilizing filter.

The third flow path 33 may be provided with a flow control valve (unillustrated) and a valve (unillustrated) for adjusting the pressure applied from the second pump 42 to the second container 12. The pressure applied from the second pump 42 to the second container 12 and the flow rate to the first container 11 may be adjusted by the second controller 72.

As long as the connection of the first container 11, the first flow path 31, the recovery container 13, the first pump 41, the second flow path 32, and the second container 12 in a closed system is maintained, a part of the components constituting the cell recovery apparatus 1 may be detachably arranged to the cell recovery apparatus 1.

In the cell recovery apparatus 1, it is preferable that a pump, especially a positive displacement pump, is not interposed between the first container 11 and the second container 12 from the viewpoint of preventing damage to the target cells.

2. Cell Recovery Method Next, a cell recovery method using the cell recovery apparatus will be described with reference to FIG. 1. Table 1 shows the operation of each component in each step.

First, while the valve 62 arranged in the second container 12 is closed, the second pump 42 is driven by the second controller 72, and pressure is applied via the third flow path 33 to the second container 12 housing the suspension containing the cells therein. By the pressure applied from the second pump 42, the suspension containing the cells is transferred from the inside of the second container 12 to the first container 11 via the second flow path 32 (Table 1, Step 1).

Then, the second pump 42 is turned off, the motor 81 is turned on, and the first container 11 is shaken by the shaker 51. In the first container 11, the suspension is filtered by the first filter 21, and the target cells are separated from the suspension (Table 1, Step 2). In addition to the shaker 51, the stirrer or the centrifuge (not shown) may be operated to perform stir and/or centrifugation.

In the first container 11, when the suspension is filtered by the first filter 21, and when the target cells are separated from the suspension, pressure may be applied to the first container 11 as appropriate to increase the filtration speed.

Thereafter, the valve 62 is opened, the first controller 71 is driven, and the separated cells are transferred from the first container 11 to the recovery container 13 by decompression suction of the first pump 41 (Table 1, Step 3). The motor 81 may then be turned on or off depending on the degree of desired separation and/or transfer of the cells.

TABLE 1

| Step | Second controller 72 | Valve 62 | Motor 81 | First controller 71 |
|---|---|---|---|---|
| 1 | ON | CLOSED | OFF | OFF |
| 2 | OFF | CLOSED | ON | OFF |
| 3 | OFF | OPEN | ON/OFF | ON |

Here, step 1 corresponds to a step of transferring suspension for transferring the suspension containing the cells from the second container 12 to the first container 11 by the second pump 42, step 2 corresponds to a step of separating the cells for separating the cells from the suspension in the first container 11, and step 3 corresponds to a step of transferring the separated cells for transferring the separated cells from the first container 11 to the recovery container 13 by decompression suction by the first pump 41.

Steps 1, 2 and 3 (i.e., the step of transferring suspension, the step of separating the cells, and the step of transferring the separated cells) are carried out in a closed system. As described above, "closed system" refers to a system that does not allow the transfer of substances (except for gas) to or from the outside beyond the boundary.

In step 2, when the target cells are separated from the suspension, the filtration rate may be increased by utilizing decompression suction by the first pump 41 and/or application of pressure by the second pump 42.

In one embodiment, wherein the cells are supported on carriers, the method further comprises a step of detaching the cells for detaching the cells from the carriers in the suspension comprising the carriers and the cells supported on the carriers. The step of detaching the cells is usually carried out in the second container 12, but may be carried out before the suspension is accommodated in the second container 12.

In one embodiment, the step of detaching the cells, the step of transferring suspension, the step of separating the cells, and the step of transferring the separated cells are carried out in this order. These steps may start the subsequent step before the end of the preceding step in addition to starting the subsequent step after the end of the preceding step, and this series of steps may be carried out simultaneously. The sequence of steps is determined on the basis of the starting point of each step.

In addition, a step of purificating the cells, a step of freezing, a step of transporting and the like may be appropriately carried out on the cells recovered in the recovery container 13.

Since the cell recovery apparatus and the cell recovery method, including the above-described configuration, can process the target cells in a closed system, the target cells can be recovered in a sterile state and the quality of the cells can be maintained. According to the cell recovery apparatus and the cell recovery method described above, the consistency of the quality is maintained by performing the prescribed operation. According to the cell recovery apparatus and the cell recovery method described above, processing of cells performed on a laboratory scale can be expanded to a commercial scale. According to the above configuration, since the processing of cells can be performed automatically without human intervention, the labor and time required for the processing can be reduced, and the consistency of the quality can be further improved by automation.

3. Cell Separation System

Figure 3:
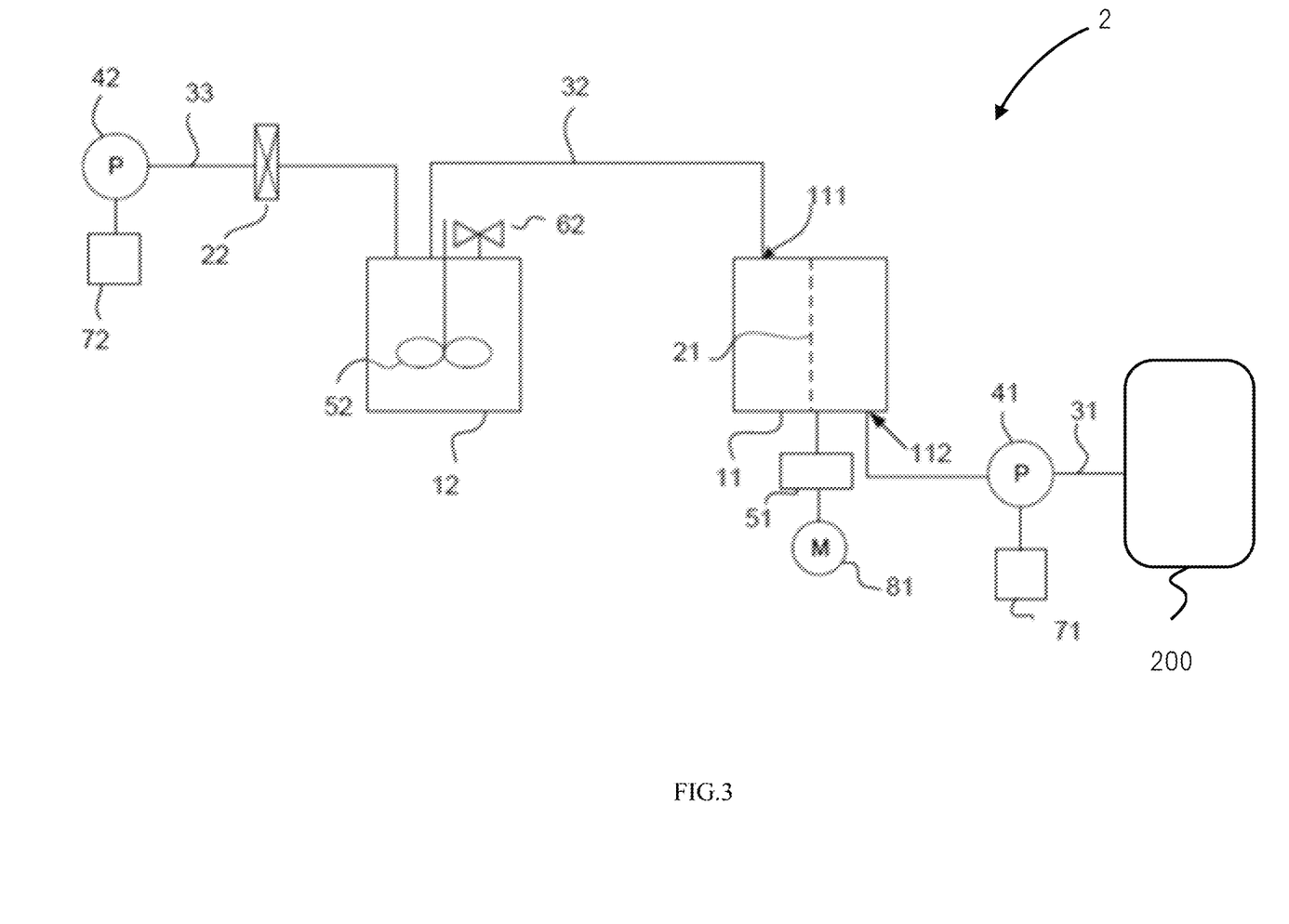
FIG. 3 is a diagram schematically showing an example of a configuration of a cell separation system according to an embodiment.
Figure 4:
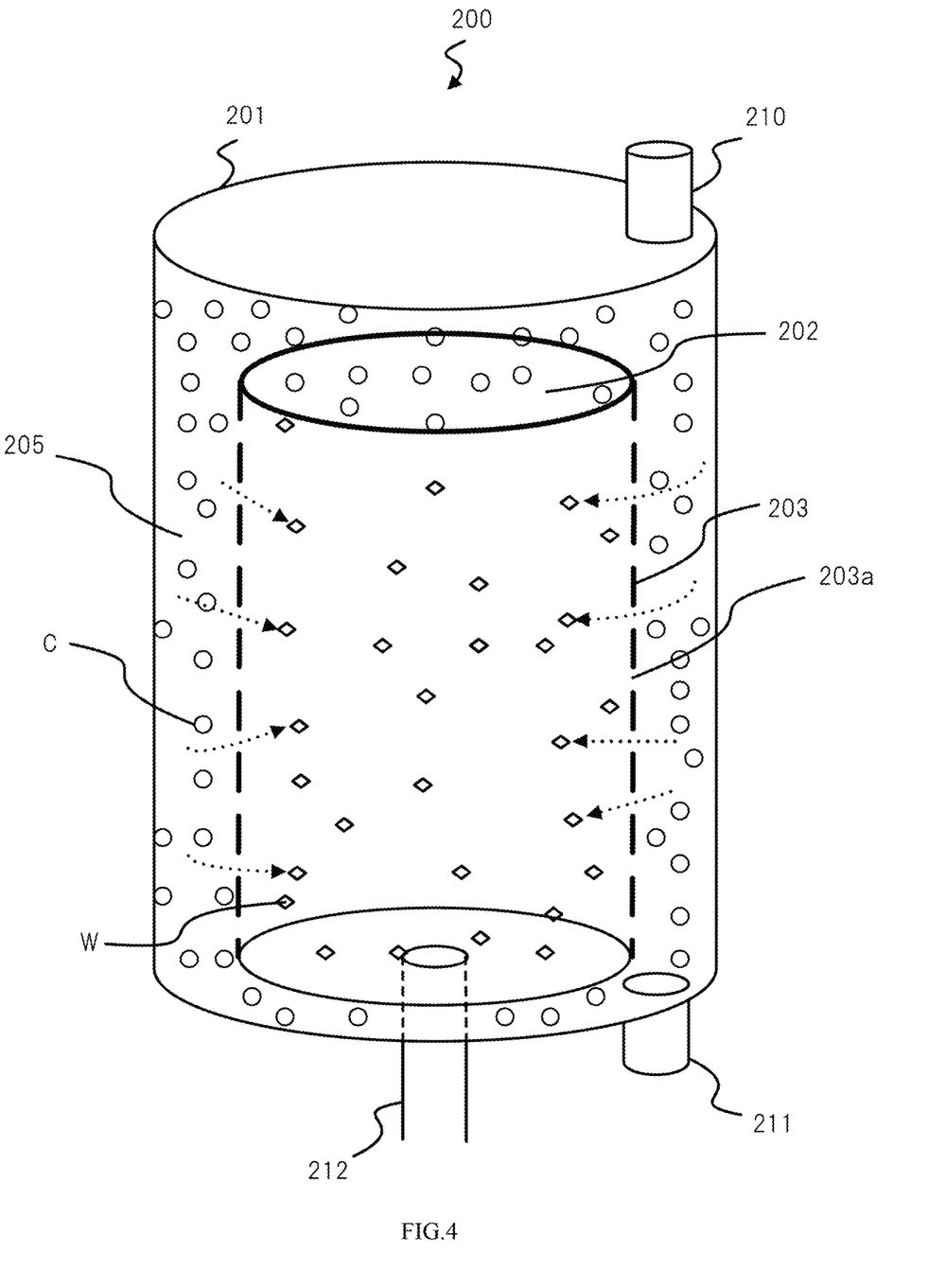
FIG. 4 is a diagram schematically showing an example of a configuration of a cell separation apparatus in a cell separation system according to an embodiment.

Next, a cell separation system according to an embodiment will be described with reference to FIGS. 3 and 4. FIG. 3 is a diagram schematically showing an example of a configuration of a cell separation system 2 according to an embodiment. FIG. 4 is a diagram schematically showing an example of a configuration of a cell separation apparatus 200 in the cell separation system 2 according to an embodiment.

The cell separation system 2, according to an embodiment, includes a cell separation apparatus 200, as shown in FIG. 3. Further, the cell separation system 2, according to an embodiment, comprises, on the upstream side of the cell separation apparatus 200, a first container 11 having a first filter 21 for separating a first removal target from suspension comprising cells and a removal target including at least the first removal target and a second removal target described below, a first flow path 31 for connecting the first container 11 and the cell separation apparatus 200, and a first pump 41 interposed in the first flow path 31 and transferring the suspension from the first container 11 to the cell separation apparatus 200 by decompression suction.

The cell separation system 2, according to an embodiment, further includes a second container 12 arranged on the upstream side of the first container 11, a second flow path 32 connecting the second container 12 and the first container 11, a second pump 42 transferring the suspension from the second container 12 to the first container 11 via the second flow path 32, and a third flow path 33 connecting the second pump 42 and the second container 12. The cell separation apparatus 200, the first container 11, the first flow path 31, the first pump 41, the second container 12, the second flow path 32, the second pump 42, and the third flow path 33 are connected in a closed system.

The first container 11, the first filter 21, the first flow path 31, the first pump 41, the second container 12, the second flow path 32, the second pump 42, and the third flow path 33 in the cell separation system 2, according to the embodiment, may be the same as those described above with reference to FIG. 1.

The cell separation apparatus 200 in the cell separation system 2, according to one embodiment, in the case of culturing cells using carriers, particularly dissolvable carriers, is capable of separating and recovering the cells with high purity by separating the removed target (in particular, the second removal target, described below) from the cells. Specifically, when cells are cultured with dissolvable carriers, the cells are first detached from the dissolvable carriers by an enzyme (for example, the trypsin described above). Next, the dissolvable carriers are dissolved in a suspension by using a dissolution method according to the type of the dissolvable carrier or the like. The method for dissolution of the dissolvable carrier is not particularly limited, and includes enzymes, photoreactions and the like. This causes a unity of a plurality of cells attached to the dissolvable carriers or an aggregate of the cultured cells to be manufactured in the suspension. The unity of a plurality of cells may be present in the suspension as sheet-like flakes or as hollow lumps such that the dissolvable carriers are "hollowed out." By providing this suspension to the cell separation apparatus 200, the cells can be separated and recovered with high purity by dividing the cell aggregates (or the cell unity) into a single cell or a small cell aggregate while separating the cell aggregates (or the cell unity) and the removal target (the second removal target).

The removal target provided to the cell separation apparatus 200 includes, in addition to the dissolvable carrier, an enzyme used for detaching the cell from the carrier, an enzyme added for dissolving the dissolvable carrier in the suspension, a protein derived from the enzyme, a dead cell, a protein contained in serum as a culture medium component, and the like. In the present disclosure, the minute removal target separated by the cell separation apparatus 200 may be referred to as the second removal target for convenience.

The dissolvable carrier may comprise, but is not limited to, at least one selected from the group consisting of cellulose, dextran, collagen, and polygalacturonic acid. The enzyme added to the suspension for dissolving the dissolvable carrier in the suspension is appropriately selected according to the type of the dissolvable carrier. Such enzymes include proteolytic enzymes, polysaccharolytic enzymes, and the like, and, for example, at least one selected from the group consisting of pectinase, collagenase, dextranase, and protease can be used. The amount of enzyme added to the suspension can be appropriately adjusted according to the type and amount of the dissolvable carriers.

As an alternative to adding enzymes, the suspension may be exposed with predetermined light so as to dissolve the dissolvable carrier in the suspension. In this case, the amount of light to be exposed, the exposure time, the type of the light source and the like can be appropriately adjusted according to the type and amount of the dissolvable carriers.

When the cells are cultured with the dissolvable carriers, the suspension, in which the cells are detached from the dissolvable carriers by an enzyme such as trypsin and the dissolvable carriers are dissolved in the suspension by an enzyme such as dextranase, can be provided to the first container 11 having the first filter 21 before or after being provided to the cell separation apparatus 200. Specifically, by providing the suspension comprising cultured cells (aggregates of cultured cells) and the removal target comprising at least the dissolvable carrier to the first container 11 having the first filter 21, a portion of the removal target contained in the suspension can be separated in the first container 11. In this case, the removal target to be separated in the first container 11 includes, for example, the dissolvable carriers which has not been dissolved by an enzyme such as dextranase, and indissolvable carriers when the dissolvable carriers and the indissolvable carriers are used in combination to culture cells. In the present disclosure, the removal target separated by the first container 11, which has relatively large (at least more granular than a single cell) particle size, may be referred to as the first removal target for convenience. However, the removal target separated in the first container 11 may include a material having a particle size smaller than that of a single cell.

As shown in FIG. 4, the cell separation apparatus 200 mainly comprises an outer cylinder 201, and an inner cylinder 202 having a side wall (second surface) 203 accommodated inside the outer cylinder 201 so as to face the outer cylinder 201 and having a large number of pores 203a formed on the side wall. The shape of the outer cylinder 201 and the inner cylinder 202 may be either a cylinder or a square cylinder. The suspension is supplied to a storage region 205 formed between an inner wall (first surface) of the outer cylinder 201 and the side wall 203 of the inner cylinder 202.

A supply port 210 and a discharge port 211 are formed in the outer cylinder 201, and the supply port 210 and the discharge port 211 can be connected in a closed system. Thus, the suspension is allowed to circulate among the supply port 210, the storage region 205 and the discharge port 211. A drain 212 is connected to the inner cylinder 202, and the separated second removal target (for example, the second removal target W shown in FIG. 4) such as the dissolvable carriers can be removed from the inner cylinder 202. A bag for recovering cells is attached to the discharge port 211, and a bag used for collecting waste liquid for recovering the second removal target or the like is attached to the drain 212.

The pore diameter of the pore 203a formed on the side wall 203 may be smaller than the pore diameter of the first filter 21, and may be appropriately selected in comparison with the pore diameter of the first filter 21, and may be, for example, 80 μm or less, 50 μm or less, 30 μm or less, or 20 μm or less. The lower limit of the pore diameter of the pore 203a is not particularly limited, and may be 0.01 μm or more, 0.5 μm or more, or 1.0 pm or more. From the viewpoint of more effectively removing the second removal target, the pore diameter of the pore 203a may be 10 μm or less, for example, 1.0 μm to 8.0 μm, preferably 2.0 μm to 6.0 μm, and more preferably 3.0 μm to 5.0 μm.

The inner cylinder 202 is relatively rotatable with respect to the outer cylinder 201. In the present disclosure, the relative rotation means that the outer cylinder 201 cannot rotate or is slowly rotated, and the inner cylinder 202 rotates at a higher speed than the outer cylinder 201. In one embodiment of the cell separation apparatus 200, the inner cylinder 202 may be rotated relative to the outer cylinder 201 at a speed, for example, within a range of 1000 rpm to 5000 rpm, preferably within a range of 1500 rpm to 4000 rpm, and more preferably within a range of 2000 rpm to 3000 rpm.

In two coaxial cylinders, it is known that a taylor couette flow is formed when fluid flows between two cylinders in a state where an inner cylinder (inner cylinder 202 in the present disclosure) rotates faster than an outer cylinder (see, e.g., Katsuhisa Matsuura, et al., Adequate taylor couette flow-mediated shear stress is useful for dissociating human iPS cell-derived cell aggregates, Regenerative Therapy vol. 12, pp. 6-13, 2019.12.15). Also in the cell separation apparatus 200 of one embodiment, if the suspension is supplied to the storage region 205 while the inner cylinder 202 is relatively rotated with respect to the outer cylinder 201, it is believed that the taylor couette flow is formed in the suspension in the storage region 205. Thus, as shown in FIG. 4, the second removal target W, such as the dissolvable carriers contained in the suspension, can be transferred from the storage region 205 to the inside of the inner cylinder 202 via the side wall 203. On the other hand, aggregate C of cells in the suspension in the storage region 205 can be split into a single cell or small aggregates of cells while remaining in the storage region 205. It should be noted that the term "taylor couette flow" in the present disclosure may mean a concept including a vortex flow or a concept including both turbulent and laminar flows.

As such cell separation apparatus 200, an apparatus capable of separating cells using a taylor couette flow can be preferably used, and, for example, those disclosed in Japanese Patent Publication No. 2015-164414 (U.S. Pat. No. 9,713,669), Japanese Patent Publication No. 2019-080562 (U.S. Patent Publication US2019/0099545), and Japanese Patent Publication No. 2019-140985 can be mentioned. The operating conditions of the cell separation apparatus 200 of the present disclosure can also be applied, for example, to the apparatus disclosed in JP Patent Publication No. 2019-080562 (U.S. Patent Publication US2019/0099545).

Conditions for separating the cells by using the taylor couette flow can be appropriately varied depending on the structure, size, mechanism, etc., of the cell separation apparatus 200. The dimension of the gap width between the first surface (inner wall of the outer cylinder 201) and the second surface (side wall 203 of the inner cylinder 202) may preferably be selected such that the taylor couette flow is generated within the gap at a desired relative rotational speed, for example, the distance of the gap width between the first surface and the second surface may be 0.05 cm to 0.30 cm, or 0.1 cm to 0.25 cm. The distance of the gap width between the first surface and the second surface may be constant or variable. The gap width can be modified by changing the outer diameter of the inner cylinder 202 and/or the inner diameter of the outer cylinder 201. The linear velocity (circumferential velocity) of the fluid generated in the gap width can be appropriately selected such that the taylor couette flow is generated in the gap and, for example, can be appropriately selected from the range of 0.58 m/s to 2.88 m/s as the circumferential velocity on the side wall surface of the inner cylinder 202. The range of the circumferential velocity is calculated based on the case where the inner cylinder 202 rotates relative to the outer cylinder 201 at a speed within the range of 1000 rpm to 5000 rpm as described above and the outer diameter of the inner cylinder 202 is set to 1.1 cm, and may be appropriately changed in accordance with a change in the outer diameter or the like of the inner cylinder 202.

In the cell separation apparatus 200, when the second removal target containing the dissolvable carriers and the cells are separated from the suspension (and splitting into aggregates into a single cell or small cell aggregates) and the cells are separated and recovered with high purity, the relative rotation of the inner cylinder 202 with respect to the outer cylinder 201 is preferably subdivided into at least two stages. Specifically, the relative rotation of the inner cylinder 202 with respect to the outer cylinder 201 can be performed in two stages: a first relative rotation performed at a first rotational speed, and a second relative rotation performed at a second rotational speed different from the first rotational speed. Thus, by setting the relative rotation to two stages, a part of the second removal target containing the dissolvable carriers can be transferred from the storage region 205 to the inside of the inner cylinder 202 in the first relative rotation, and the remainder of the second removal target can be transferred from the storage region 205 to the inside of the inner cylinder 202 in the second relative rotation. Thus, the single cell or small aggregates of cells can be separated and recovered with high purity.

In addition, by setting the relative rotation of the inner cylinder 202 with respect to the outer cylinder 201 to two stages as described above, it is possible to facilitate the splitting of the aggregate C of cells into the single cell or small aggregates of cells in the first relative rotation. Thus, the second removal target can be efficiently transferred to the inside of the inner cylinder 202 by the second relative rotation. In this case, by removing the clogging of the pore 203a formed on the side wall 203 caused by the aggregate C of the cells after the first relative rotation and before the second relative rotation, the separation function of the second removal target by the second relative rotation can be made more efficient.

The first relative rotation is carried out before the second relative rotation, and the first rotational speed is preferably set faster than the second rotational speed. The first rotational speed may be, for example, in the range of 2500 rpm to 5000 rpm, preferably in the range of 2700 rpm to 3500 rpm. The second rotational speed may be, for example, in the range of 1000 rpm to 3000 rpm, preferably in the range of 2000 rpm to 3000 rpm.

When the first rotational speed is faster than the second rotational speed, the execution time for performing the first relative rotation is preferably shorter than the execution time for performing the second relative rotation. Thus, the time for the cells (aggregates of cells) contained in the suspension to stay in the fluid rotating at the first rotational speed can be shortened, the cells to be separated and recovered can be prevented from being damaged or killed—in other words, the separation and recovery efficiency of the cells can be increased. From another viewpoint, the number of times the suspension is subjected to the first relative rotation is preferably one (the suspension emitted from the discharge port 211 is not supplied again from the supply port 210 into the storage region 205), and the number of times the suspension is subjected to the second relative rotation is preferably multiple times (the suspension emitted from the discharge port 211 is supplied again from the supply port 210 into the storage region 205).

The processing temperature at which the suspension is subjected to the first relative rotation and the second relative rotation can be suitably set, for example, 20° C. to 50° C. or 30° C. to 40° C. The total time for subjecting the suspension to the first relative rotation and the second relative rotation can be appropriately set depending on the type of cells, the rotational speed of the inner cylinder 202, and the like, but may be, for example, in the range of 10 seconds to 60 minutes, preferably in the range of 1 minute to 30 minutes.

Even in the case of culturing cells by using an indissolvable carriers, it is useful to apply the cell separation apparatus 200 in the cell separation system 2 according to one embodiment. Enzymes are added to the suspension to detach cells from the indissolvable carriers, resulting in aggregates or unities of cells in the suspension. By providing this suspension to the cell separation apparatus 200, aggregates of cells or unities of cells can be effectively separated into a single cell, and a removal target (a second removal target) contained in the suspension can be effectively separated.

The cell separation system 2 includes the first container 11 having the first filter 21 and the cell separation apparatus 200, and can efficiently separate the first removal target and the second removal target from the cells by respective different mechanisms while making the pore diameter of the first filter 21 different from the pore diameter of the pore 203a in the cell separation apparatus 200.

The relative movement between the first surface (for example, the inner wall of the outer cylinder 201) and the second surface (for example, the side wall 203 of the inner cylinder 202) in the cell separation apparatus 200 is not limited to the relative rotation described above, and may be a parallel movement substantially maintaining the opposing distance between the first surface and the second surface, or a vertical movement varying the opposing distance between the first surface and the second surface. The relative movement may be performed continuously or intermittently (discontinuously).

According to the cell separation system 2 related to the present embodiment, the first removal target and the second removal target can be efficiently removed from the cell suspension in the culture container to harvest the cells. As a result, the cells to be recovered can be efficiently concentrated to high purity, for example, the target cells increased in a culture container of 10 L, 20 L, 30 L, 40 L, 50 L or more volumes can be recovered as a cell suspension of 10 L, 1 L, 500 mL or less volumes. The concentration ratio (volume in the culture container/volume after recovery) of the recovered cell suspension can be, for example, 5 times or more, 50 times or more, 100 times or more, or 200 times or more. The final cell density in this case may be, for example, $1\times10^5$/mL or more, $1\times10^6$/mL or more, or $1\times10^7$/mL or more.

EXAMPLES

Hereinafter, the present disclosure will be described more specifically by way of examples, but the present disclosure is not limited in any way by these examples.

Example 1

(1) Culture of Cells
Stem cells were supported to microcarriers (200 μm diameter, Synthemax II coating dissolvable microcarrier, Corning Inc.) and cultured in a suspension with agitation in a 2L bioreactor (Univessel SU, Sartorius AG) containing a culture bag with a stirring blade.

Agitation of the 2L bioreactor was then stopped and left to stand for 10 minutes, after the microcarriers had completely settled, about 1.6 L of the supernatant was removed.

(2) Washing
1.0 L of PBS (-) was added to the 2L bioreactor, and the 2L bioreactor was agitated at a rotational speed of 80 rpm for 10 minutes. Agitation was stopped and the supernatant was removed after the microcarrier had completely settled. At this time, about 0.4 L of the suspension remained in the 2L bioreactor. This washing was carried out twice.

(3) Enzyme Treatment and Cell Removal
0.4 L of two-fold concentration trypsin enzyme solution ("TrypLE (2x)," Thermofisher) was added, and the bioreactor was agitated at 37° C. at 90 rpm for 20 minutes to detach cells from the microcarriers.

(4) Enzyme Activation
0.4 L of alphaMEM/20% FBS was added. At this time, 31.2 L of the suspension was contained in the bioreactor.

(5) Separation of the Cells
In the 2L bioreactor, while agitation at 80 rpm so as to disperse beads (microcarrier) uniformly, an air pump (Azwan Company) was driven as the second pump so as to provide a liquid delivery speed of less than 2.5 L/min, and the suspension was transferred to a microcarrier separator equipped with a mesh having a pore diameter of 50 pm. Then, another 300 ml of PBS (-) was added to the 2 L bioreactor to make the suspension washed, and the suspension was transferred to the microcarrier separator.

After transferring, the air pump was stopped, and the microcarrier separator was gently shaken from side to side in a horizontal state to allow the cells that had not passed through the filter to do so.

After separation of the cells, a positive displacement peristaltic pump (Cole Parmer Model Number 07522-20) was driven as the first pump to transfer the cell suspension to the recovery bag at a delivery rate of less than 2.5 L/min.

(6) Purification
The cell suspension containing the cells separated from the microcarriers in the separation step was transferred to a purifier equipped with a mesh having a pore diameter of 4 μm to remove contaminants of 4 μm or less, and the cell suspension was purified. The purifier in this case is the cell separation apparatus 200 described above, and the cell separation apparatus in Example 2 described later can be used.

In this example, sizes of the cells and microcarriers were 12 μm to 16 μm and 200 μm, respectively.

Example 2

(1) Culture of Cells
Stem cells were supported to microcarriers (200 μm diameter, Synthemax II coating dissolvable microcarrier, Corning Inc.) in a 2L bioreactor containing a culture bag with a stirring blade and suspended with agitation. After confirming that the number of cultured cells reached a predetermined target number, the culture was ended.

(2) Washing
1.0 L of PBS (-) was added to the 2L bioreactor, and agitation was carried out at a rotational speed of 80 rpm for 10 minutes. Agitation was stopped and the supernatant was removed after the microcarrier had completely settled. This washing was carried out twice.

(3) Cell Detachment and Dissolution of Dissolvable Microcarriers (Enzyme Treatment)
The enzyme (havest solution prepared with TrypLE (1x): 238.4 ml, Pectinase: 6.6 ml and EDTA: 5.0 ml) pre-warmed to 37° C. was added to the 2 L bioreactor and the 2 L bioreactor was agitated at 85 rpm for 10 to 15 minutes. A portion of the culture was then taken from the 2 L bioreactor, and it was confirmed that the cells were detached from the microcarriers and that the microcarriers were dissolved in the culture by phase contrast microscopy. In addition, cells (aggregates of cells) with a hollow structure formed by dissolving the microcarriers in the culture medium by the enzyme was obtained.

(4) Cell Separation (Removal of the Dissolved Microcarriers, etc.)
After the suspension containing the aggregates of cells with a hollow structure obtained by (3) above was filled in a blood separation bag, the blood separation bag was then connected to the supply port of the cell separation apparatus, and an empty bag for recovery was connected to the discharge port, then the suspension was supplied to the storage region arranged between the outer cylinder and inner cylinder in the cell separation apparatus. The drain of the cell separation apparatus was connected to an empty bag for recovering the removal target. Then, the flow rate of the (at the supply port) suspension when supplied to the storage region was set to 140 ml/min, and the flow rate of the (at the discharge port) suspension when discharged was set to 27 ml/min, and the inner cylinder was rotated with respect to the outer cylinder at a rotational speed of 2700 rpm to 3500 rpm, then the aforementioned first relative rotation was carried out. A LOVO (registered trademark) cell treatment apparatus (Fresenius Kabi Japan K.K.) was used as the cell separation apparatus.

Then, after the treatment based on the first relative rotation, various parts in the cell separator apparatus were replaced as needed, and the aforementioned second relative rotation was carried out by adjusting the flow rate of the suspension (at the supply port) when supplied to the storage region to 100 ml/min, and the flow rate of the suspension (at the discharge port) when discharged to 35 ml/min, and rotating the inner cylinder relative to the outer cylinder at a rotational speed of 2000 rpm to 3000 rpm (first round of the second relative rotation). Next, the flow rate of the (at the supply port) suspension when supplied to the storage region was set to 100 ml/min, and the flow rate of the (at the discharge port) suspension when discharged was adjusted to 10 ml/min, and the inner cylinder was rotated relative to the outer cylinder at a rotational speed of 2000 rpm to 3000 rpm, then the second round of the second relative rotation was carried out. That is, in the second embodiment, the second relative rotation was carried out twice.

(5) Result

In a series of Example 2, the washing efficiency after the first relative rotation was confirmed to be about 81%. Here, the washing efficiency in this case is understood as the removal rate of the removal target such as the dissolvable carrier contained in the suspension before the first relative rotation.

On the other hand, the washing efficiency after all of relative rotation of the first relative rotation, first round of the second relative rotation, and second round of the second relative rotation was confirmed to be 99.76%. Here, the washing efficiency in this case should be understood in the same manner as described above.

Figure 5A:
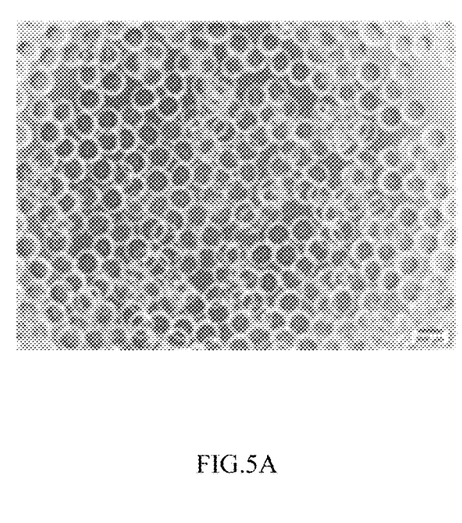
FIG. 5A is a photomicrograph of cells cultured on dissolvable carriers.
Figure 5B:
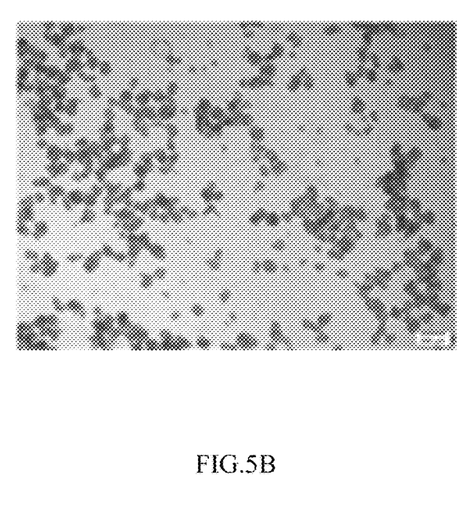
FIG. 5B is a photomicrograph of an aggregate of cells with a hollow structure.
Figure 5C:
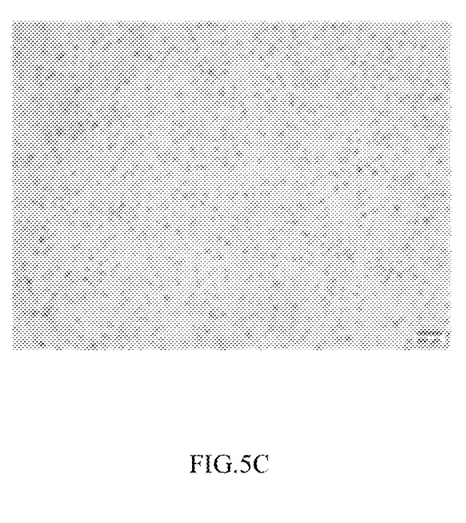
FIG. 5C is a photomicrograph of cells separated and recovered by a cell separation system according to an embodiment.

Also, the manner in which the cells separated and recovered by a series of this Example 2 are split into single cells or small aggregates of cells will be described with reference to FIGS. 5A-5C. FIG. 5A is a photomicrograph of cells cultured on dissolvable carriers. FIG. 5B is a photomicrograph of an aggregate of cells with a hollow structure. FIG. 5C is a photomicrograph of cells separated and recovered by a cell separation system 2 according to an embodiment.

Referring to FIG. 5C, it is understood that the cells are predominantly subdivided and split compared to the photomicrographs of FIGS. 5A and 5B.

As described above, based on the cell separation system 2 according to one embodiment, it is possible to efficiently separate cell aggregates and the removal target, and efficiently split cell aggregates into a single cell or small aggregates of cells, resulting in separation and recovery of the cells with high purity.

Although various embodiments have been exemplified as described above, the above embodiments are merely examples and are not intended to limit the scope of the invention. The above embodiments can be carried out in various other configurations, and various omissions, substitutions, and changes can be made without departing from the gist of the invention.

In the present disclosure, any numerical range expressed by using "to" indicates a range including the numerical values before and after "to" as a minimum value and a maximum value, respectively. In the numerical ranges described in the present disclosure in stages, the upper limit or lower limit of the numerical range of one stage may be optionally combined with the upper limit or lower limit of the numerical range of another stage.

This present application is based on the following Japanese patent applications, which benefit from the priority of the Japanese patent applications. The following Japanese patent application is incorporated by reference in its entirety as if set forth fully herein.

(1) Japanese Patent Application No. 2020-42322, filed on Mar. 11, 2020, titled "Cell recovery apparatus and cell recovery method"

All documents, patent applications, and technical standards described in this present disclosure are incorporated by reference in their entirety as if set forth fully herein.

The invention claimed is:

1. A cell separation system at least comprising:
   a first container having a first filter for separating a first removal target from a suspension comprising cells and a removal target including at least the first removal target and a second removal target;
   a cell separation apparatus;
   a first flow path connecting the first container and the cell separation apparatus; and
   a first pump interposed in the first flow path for transferring the suspension from the first container to the cell separation apparatus by decompression suction,
   a second container disposed on the upstream side of the first container;
   a second flow path connecting the second container and the first container;
   a second pump for transferring the suspension from the second container to the first container via the second flow path; and
   a third flow path connecting the second pump and the second container;
   wherein the first container, the first flow path, the cell separation apparatus, the first pump, the second container and the second flow path are connected in a closed system, p1 wherein the cells are supported on carriers in the suspension;
   wherein the cells are detached from the carriers in the second container;
   wherein the cells and the carriers are separated by the first filter, and
   wherein the cell separation apparatus comprises an outer cylinder, and an inner cylinder accommodated inside the outer cylinder having a side wall on which a large number of pores are formed, and wherein the cell separation apparatus is configured to separate the second removal target and the cells in a storage region between an inner wall of the outer cylinder and the side wall of the inner cylinder.

2. The cell separation system as claimed in claim 1, wherein the first pump is a positive displacement pump.

3. The cell separation system as claimed in claim 1, wherein the second removal target includes at least a dissolvable carrier.

4. The cell separation system as claimed in claim 1, wherein the cell separation apparatus separates the cells by relatively rotating the inner cylinder to the outer cylinder and transferring the second removal target from the storage region to the inside of the inner cylinder via the side wall.

5. The cell separation system as claimed in claim 4, wherein the relative rotation includes a first relative rotation performed at a first rotational speed and a second relative rotation performed at a second rotational speed different from the first rotational speed.

6. The cell separation system as claimed in claim 5, wherein the first rotational speed is faster than the second rotational speed.

7. The cell separation system as claimed in claim 4, wherein pore diameter of the large number of pores formed on the side wall are smaller than pore diameter of the first filter.

8. The cell separation system as described in claim 1, wherein the first container comprises at least one selected from the group consisting of a shaker, a stirrer, and a centrifuge.

9. The cell separation system as described in claim 1, wherein the second container comprises at least one selected from the group consisting of a shaker and a stirrer.

10. The cell separation system as described in claim 1 further comprising a second filter interposed in the third flow path.

11. The cell separation system as described in claim 1, wherein the second filter comprises a pore having a diameter in the range of 0.01 μm to 30 μm.

12. The cell separation system as described in claim 1, wherein a flow rate of the first flow path is in the range of 0.0004 L/min to 8.0 L/min.

13. The cell separation system as described in claim 1, wherein the first flow path has an inner diameter in the range of 1.8 mm to 13.0 mm.

14. A cell separation method using the cell separation system of claim 1, comprising:
   separating the first removal target from the suspension provided in the first container having a first filter, wherein the suspension comprises cells and a removal target including at least the first removal target and a second removal target;
   supplying the suspension to a storage region in the cell separation apparatus configured between a first surface and a second surface facing the first surface on which a large number of pores are formed; and
   separating the cells from the suspension by moving one of the first surface and the second surface relative to the other.

15. The cell separation method as claimed in claim 14, wherein the separation of the cells includes rotating one of the first surface and the second surface relative to the other so as to transfer the second removal target in the suspension to the outside of the storage region via the second surface and leave the cells in the storage region.

16. The cell separation method as claimed in claim 14, wherein the separation of the cells includes:
   transferring a portion of the second removal target to the outside of the storage region by rotating one of the first surface and the second surface relative to the other at a first rotational speed; and
   transferring the remainder of the second removal target to the outside of the storage region by rotating one of the first surface and the second surface relative to the other at a second rotational speed.

17. The cell separation method as claimed in claim 16, wherein the first rotational speed is faster than the second rotational speed.

18. The cell separation method as claimed in claim 14, further comprising transferring the suspension from the first container to the cell separation apparatus by decompression suction of a first pump.

19. The cell separation method as claimed in claim 14, wherein the second removal target includes at least a dissolvable carrier.

* * * * *